(12) United States Patent
Vogele

(10) Patent No.: US 12,714,592 B2
(45) Date of Patent: Aug. 25, 2026

(54) PATIENT IMMOBILIZATION DEVICE, SYSTEM AND METHOD FOR IMMOBILIZING A PATIENT

(71) Applicant: ISYS MEDIZINTECHNIK GMBH, Kitzbühel (AT)

(72) Inventor: Michael Vogele, Schwabmünchen (DE)

(73) Assignee: ISYS MEDIZINTECHNIK GMBH, Kitzbühel (AT)

( * ) Notice: Subject to any disclaimer, the term of this patent is extended or adjusted under 35 U.S.C. 154(b) by 782 days.

(21) Appl. No.: 17/603,489

(22) PCT Filed: Apr. 24, 2020

(86) PCT No.: PCT/EP2020/061563
§ 371 (c)(1),
(2) Date: Oct. 13, 2021

(87) PCT Pub. No.: WO2020/216951
PCT Pub. Date: Oct. 29, 2020

(65) Prior Publication Data

US 2022/0211535 A1 Jul. 7, 2022

Related U.S. Application Data

(60) Provisional application No. 62/839,420, filed on Apr. 26, 2019.

(51) Int. Cl.
*A61F 5/37* (2006.01)

(52) U.S. Cl.
CPC .................................. *A61F 5/3776* (2013.01)

(58) Field of Classification Search
CPC .... A61F 5/3776; A61F 5/3784; A61F 5/3769; A61F 5/37; A47G 9/02; A61B 6/0421;
(Continued)

(56) References Cited

U.S. PATENT DOCUMENTS 3,881,476 A 5/1975 Bolker et al.
4,180,879 A * 1/1980 Mann .................... A61F 5/3784 5/621

(Continued)

FOREIGN PATENT DOCUMENTS

CN 103536421 A 1/2014
CN 208677681 U 4/2019

(Continued)

*Primary Examiner* — Ophelia A Hawthorne
(74) *Attorney, Agent, or Firm* — Birch, Stewart, Kolasch & Birch, LLP

(57) ABSTRACT

The invention relates to a patient immobilization apparatus (100) comprising a planar element (105) made of a non-woven fabric. The planar element (105) has an elongate middle section (110) and a plurality of arms (120; 130), which extend out laterally on both sides of the middle section (110). The patient immobilization apparatus (100) can be provided to the end user, preferably in a folded state. In the folded state, each of the arms (120; 130) is folded laterally on the elongate middle section (110). Parts of the elongate middle section (110), having the arms (120; 130) folded laterally thereon, are advantageously additionally foldable onto each other in the longitudinal direction. Each arm (120; 130) can be folded laterally in part on itself before it is folded laterally on the elongate middle section (110).

21 Claims, 7 Drawing Sheets

(58) Field of Classification Search
CPC ... A61G 13/101; A61G 7/1023; A61G 7/1026
See application file for complete search history.

(56) References Cited

U.S. PATENT DOCUMENTS

| | | | | |
|---|---|---|---|---|
| 4,908,889 | A | 3/1990 | Lonardo | |
| 5,392,973 | A * | 2/1995 | Benson | A45F 5/00 224/625 |
| 5,626,397 | A * | 5/1997 | Reid | A61F 5/3784 297/229 |
| 5,944,016 | A * | 8/1999 | Ferko, III | A61F 5/05883 128/869 |
| 2001/0005779 | A1* | 6/2001 | Laughlin | B29C 65/7441 602/23 |
| 2006/0137693 | A1* | 6/2006 | Lewis | A61B 46/00 128/853 |
| 2008/0201915 | A1* | 8/2008 | Obiols | F16L 3/233 24/306 |
| 2008/0238174 | A1* | 10/2008 | Cinquanta | B60N 2/882 24/442 |
| 2016/0235579 | A1 | 8/2016 | Tao et al. | |
| 2017/0246024 | A1 | 8/2017 | Vogele | |

FOREIGN PATENT DOCUMENTS

| | | | |
|---|---|---|---|
| JP | 50-27377 | A | 3/1975 |
| JP | 2001-20643 | A | 1/2001 |
| JP | 2003-231464 | A | 8/2003 |
| JP | 2016-533233 | A | 10/2016 |
| JP | 2017-525421 | A | 9/2017 |

* cited by examiner

101

PATIENT IMMOBILIZATION DEVICE, SYSTEM AND METHOD FOR IMMOBILIZING A PATIENT

The invention relates to a patient immobilization device and also to a system and a method for immobilizing a patient, in particular while a medical procedure is being carried out.

PRIOR ART

In many medical procedures, it is necessary that a patient does not move a part of the body on which the medical procedure is being carried out. Medical procedures that require immobilization of the patient include, for example, diagnostic and therapeutic radiology, radiation therapy, operative/surgical procedures, and pre- or post-operative care.

In the applicant's published patent application US 2017/0246024 A1, the disclosure of which is hereby incorporated by reference in its entirety, a simple device for immobilizing the human body or parts of the body is disclosed. The device has at least one immobilizing element that can be positioned on the body surface. The immobilizing element consists of a bonded, nonwoven fabric that can be fastened using a micro-hook and loop fastener.

The object of the invention is to make available an improved patient immobilization device in conjunction with a system and a method that allows even simpler and more flexible handling.

DISCLOSURE OF THE INVENTION

An improved patient immobilization device comprises a planar element made of nonwoven fabric. The planar element has an elongate middle part and a multiplicity of arms which extend laterally on both sides from the middle part. A particularly flexible and, if necessary, large-area immobilization of patients and parts of their body is made possible using a plurality of arms. A plurality or multiplicity of arms is to be understood here as numbering at least two arms on both sides of the middle part.

The patient immobilization device can be made available to the end user particularly advantageously in a folded state. In the folded state, each of the arms is folded laterally onto the elongate middle part. Parts of the elongate middle part, with the arms folded laterally thereon, are moreover preferably folded onto one another in the longitudinal direction. In addition, each arm can preferably also be folded laterally onto itself before being folded laterally onto the elongate middle part. Overall, the various folding options result in a compact package that is easy to handle even for large-area uses.

A system for immobilizing a patient comprises the patient immobilization device and a multiplicity of micro-hook fastening elements which are fastenable to the sides of a patient table. One or more arms of the patient immobilization device can be held by micro-hooks which are arranged on parts of the micro-hook fastening elements.

The micro-hook fastening elements preferably comprise a plate-shaped part with a multiplicity of micro-hooks arranged thereon. The micro-hook fastening element moreover comprises an upper web and a lower web. The upper web and the lower web are configured and spaced apart such that a rail of a patient table can be clamped between them. The lower web can include a channel, which is configured such that it receives a lower part of the rail of the patient table, and also a deformable rubber strip which is arranged in the channel.

In an advantageous development of the system according to the invention, provision is made that disposable patches can be arranged between the patient immobilization device and the micro-hook fastening elements. The disposable patches have fabric loops on the inner face and micro-hooks on the outer face. The disposable patches can be used in a sandwich structure between the micro-hook fastening elements and the planar element of nonwoven fabric of the patient immobilization device.

An alternative micro-hook fastening element comprises a keder cord and a micro-hook patch wrapped around the keder cord. The keder cord can have a lower part with a cross-sectional diameter greater than the diameter of a keder rail slot of a patient table, and an upper part with a width that is smaller than the diameter of the keder rail slot of the patient table. The upper part of the keder cord can optionally be bent between 45 and 90 degrees in its region guided through the keder rail slot.

Each of the micro-hook fastening elements can be provided with a removable disposable patch that engages in the micro-hooks of the micro-hook fastening elements. The removable disposable patch can be provided in order to protect the micro-hooks before use or to prevent direct contact between the micro-hooks and the patient.

A method for securing a patient on a patient table can be based on the provision of the patient immobilization device. The patient immobilization device is placed onto the patient, and two or more arms of the patient immobilization device are fastened to micro-hook fastening elements on opposite sides of the patient table. The method can moreover include selectively removing a part of the patient immobilization device in order to create an access opening for performing a medical intervention on the patient. For this purpose, the patient immobilization device preferably has perforations at which individual arms and/or parts of the middle part can be completely or partially separated.

The following detailed description of the invention is of a purely illustrative nature and is not intended to limit the invention or the application and uses of the invention. There is also no intention to be bound to a theory presented in the preceding background of the invention or in the following detailed description of the invention.

EMBODIMENTS OF THE INVENTION

Figure 1:
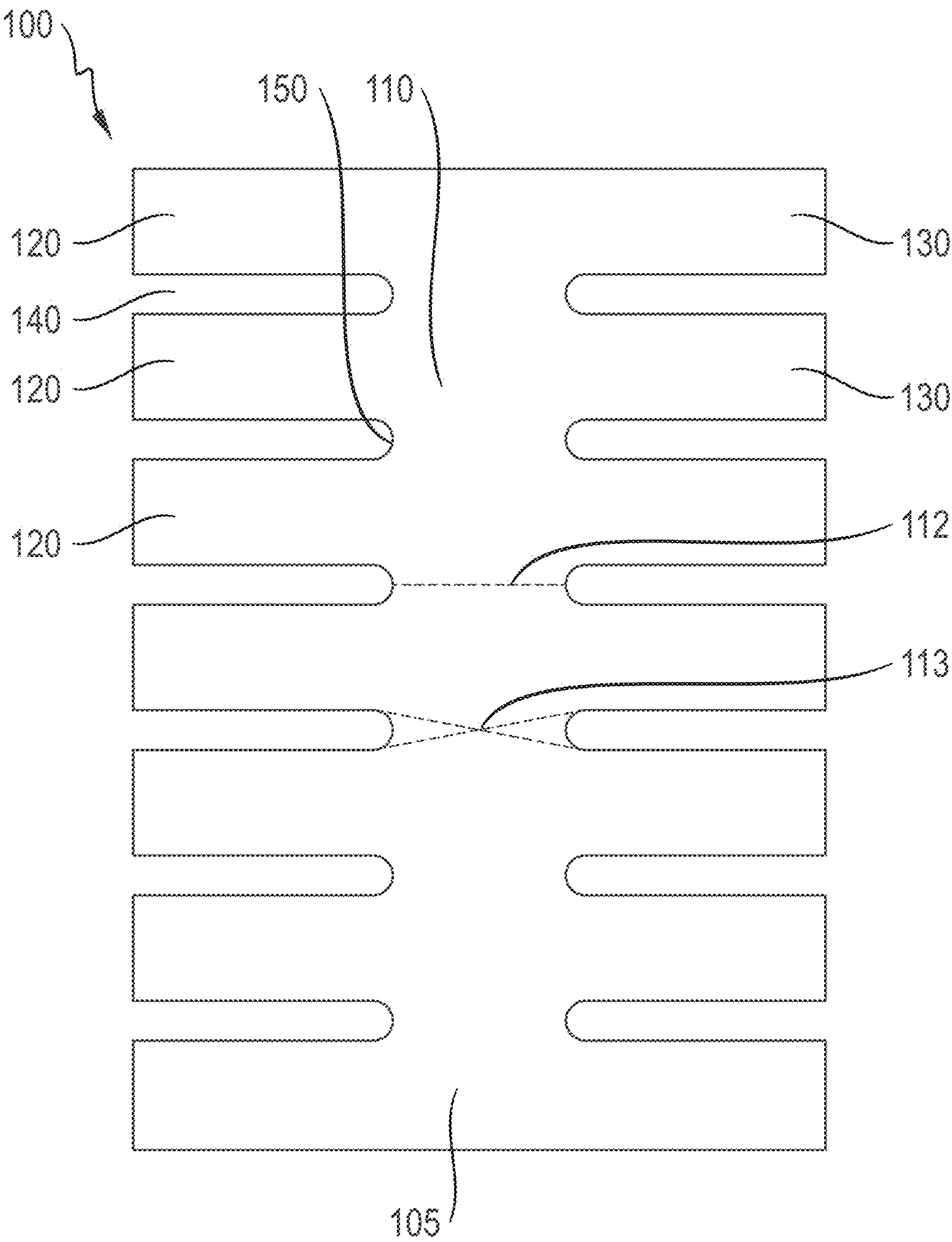
FIG. 1 shows a flat view of a patient immobilization device.

Referring to FIG. 1, a nonwoven fabric layer forming a planar element 105 is shaped to provide a patient immobilization device 100. The immobilization device 100 has an elongate middle part 110, from which two or more arms 120, 130 extend laterally on both sides of the middle part 110. The fabric of the planar element 105, or the non-woven fabric layer, can preferably be produced from nonwoven polypropylene with a thickness of approximately 1 mm, preferably of approximately 0.8 mm. To achieve the desired strength, the fabric should preferably have a tensile strength of more than 100 N per 50 mm fabric width. The fabric is radioparent and MR (magnetic resonance tomography) safe. It can be sterilized with steam or ethylene oxide according to the standards ISO 11135, ISO 10993-7 or EN 1422.

Figure 4:
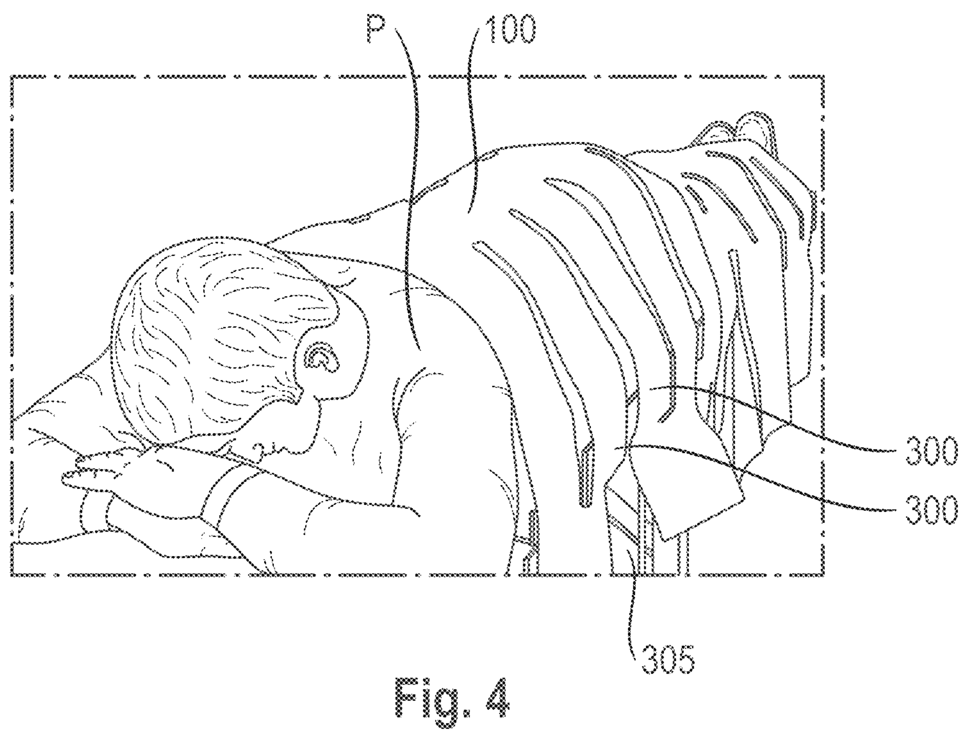
FIG. 4 shows the patient immobilization device from FIG. 1 in use on a patient lying on a patient table.

As is shown in FIG. 4, the patient immobilization device can be used to secure a patient P to a patient table 305 by placing the middle part 110 on the patient's torso and fastening the arms 120, 130 to micro-hook fastening elements 300, which can be fastened on each side of the patient table 305. Other uses of the patient immobilization device 100 are possible. These include immobilizing a body part of a patient P with the patient immobilization device 100 similarly to a bandage or a plaster cast, possibly together with one or more rigid, elongate elements, for example when splinting a bone fracture.

The elongate middle part 110 is preferably between 100 cm and 200 cm long and has a width of between 10 cm and 30 cm. The elongate middle part 110 may be suitable for covering a substantial part of the torso of a patient P, such that it is possible to apply uniform pressure to the torso without creating local pressure points.

The arms 120, 130 are preferably between 5 cm and 20 cm wide and between 50 cm and 150 cm long. The elongate middle part 110 is generally longer than the arms 120, 130 and often has approximately the same width as the arms 120, 130. Longitudinal gaps 140 can be cut out between every two adjacent arms 120, 130. The longitudinal gaps 140 can be between 1 cm and 10 cm wide.

The longitudinal gaps 140 can be cut out with semicircular transitions 150 which separate the arms 120, 130 at the middle part 110. This reduces the risk of accidentally tearing the fabric sheet.

The arms 120, 130 can be arranged symmetrically, with a left arm 120 in each case being arranged on the middle part 110 symmetrically with respect to a right arm 130. The patient immobilization device 100 can have between five and fifteen arms 120, 130 which extend laterally on each side of the middle part 110.

In use, each arm 120, 130 can be individually and separately fastened to a micro-hook fastening element 300. In this case, the number of micro-hook fastening elements 300 that are used on each side of patient P is equal to the number of arms 120, 130 on that side of the patient P. Alternatively, an n:1 or 1:n relationship between arms 120, 130 and micro-hook fastening elements 300 can be used. That is to say, one fastening element 300 can be used to fasten two or more arms 120, 130, or one arm 120, 130 can be fastened to two or more micro-hook fastening elements 300.

The arms 120, 130 and the corresponding micro-hook fastening elements 300 are preferably configured such that they withstand a tensile force of at least 40 N.

In order to permit access to a specific body part of a patient P, one or more arms 120, 130 can remain unsecured or can even be separated from the central portion 110, so as to create an accessible region while a medical intervention is being performed. The nonwoven fabric of the planar element 105 of the patient immobilization device 100 can be cut, for example, with a safety cutting device having a blade located in a narrow slot into which an arm 120, 130 of the patient immobilization device 100 can be inserted, but which is inaccessible to a human finger or another body part.

Perforations 112, 113 can be formed within the middle part 110 in order to make the middle parts 110 of the patient immobilization device 100 easy to separate. As is shown, the perforations 112 can run perpendicular to the longitudinal axis of the middle part 110 between two arms 120, 130. The perforations 112 preferably extend parallel to the holding force of the patient immobilization device along the arms 120, 130. As a result, the perforations 112, 113 do not weaken the ability of the device to hold a patient P securely. However, the perforations 112, 113 offer an additional safety mechanism in the event that an arm 120, 130 has been fixed wrongly or with too high a tensile force, for example by being wrongly clamped. In this case, the loose arm 120, 130 can be pulled in any direction, without the risk of the remaining arms 120, 130 being accidentally removed. The central portion 110, also referred to as the middle part 110, tears along the perforations 112, 113, such that no force exerted on an individual arm 120, 130, regardless of its direction, can cause the detachment of an adjacent arm 120, 130.

To promote this safety aspect, the perforations 113 in the middle part 110 of the patient immobilization device 100 can run tangentially from the arms 120, 130 in an X-shaped pattern over the middle part 110.

Figures 2, 3:
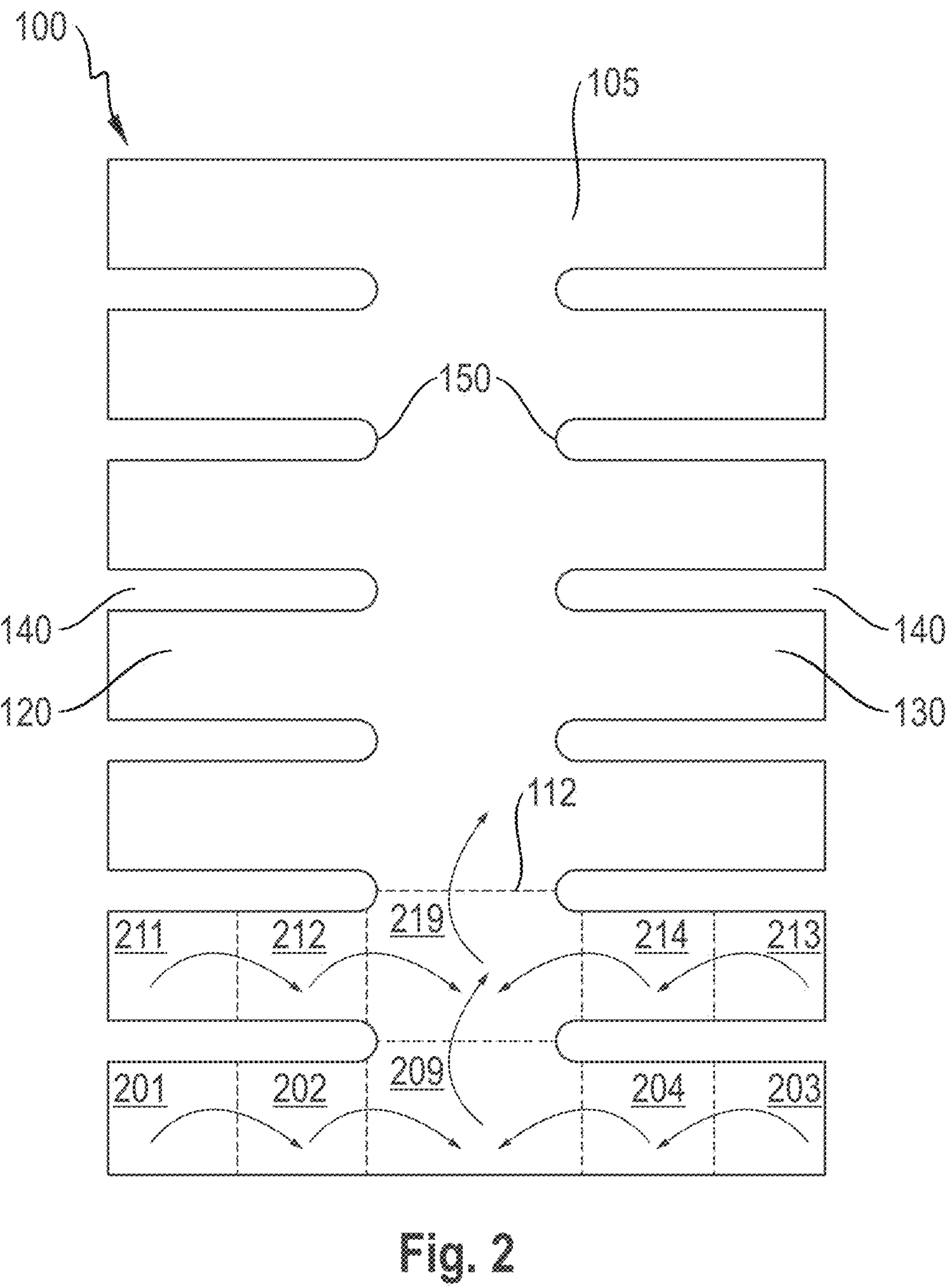
FIG. 2 shows the folding-up of a patient immobilization device according to FIG. 1.
FIG. 3 shows the patient immobilization device according to FIGS. 1 and 2 in the folded state.

The patient immobilization device 100 is preferably shipped in the folded state 101, as shown in FIG. 3, and made available for use by medical personnel at the place of use. As is shown in FIG. 2, the folded state 101 can be obtained by folding each arm 120, 130 onto itself one or more times, as is indicated by the arrows 201, 202 and 203, 204. The arm 120, 130, pre-folded in this way, is then folded onto the middle part 110. As is indicated by arrows 209, 219, the folded arms 120, 130, and a part of the central part 110 lying correspondingly under them, can then be folded, according to the arrow 209, onto the next arms 120, 130, which are pre-folded according to the arrows 211, 212 or 213, 214, and the adjacent part of the middle part 110. The longitudinal fold can preferably coincide here with the perforations 112. The folding process allows the medical personnel to easily place the folded patient immobilization device 101 centrally onto the torso of the patient P and then to unfold it there, as is shown in FIG. 4. During the unfolding, the medical personnel can fasten the arms 120, 130 to corresponding micro-hook fastening elements 300, which can be easily fastened on both sides of the patient P to a bed or patient table 305. In this way, the patient is quickly and increasingly immobilized without the need for any complicated cuts to be made in the fabric.

Figure 5:
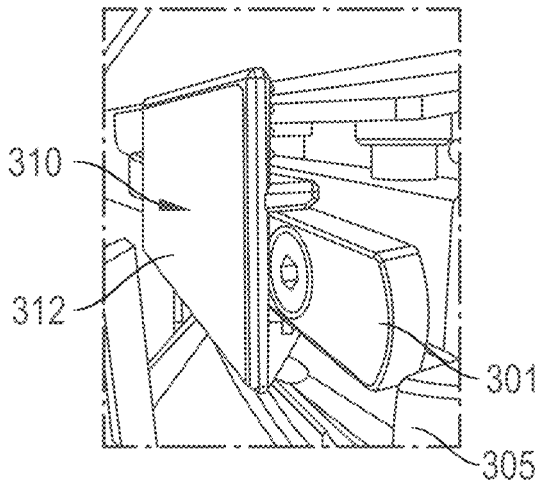
FIG. 5 shows a perspective front and side view of a micro-hook fastening element for a system for patient immobilization, which is fastened to a rail of a patient table.
Figure 6:
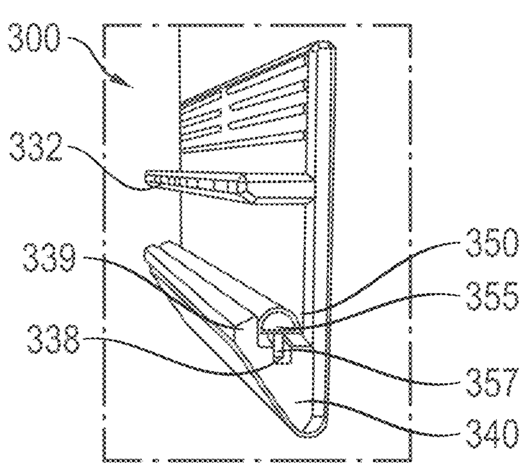
FIG. 6 shows a perspective rear and side view of a micro-hook fastening element according to FIG. 5.
Figure 7:
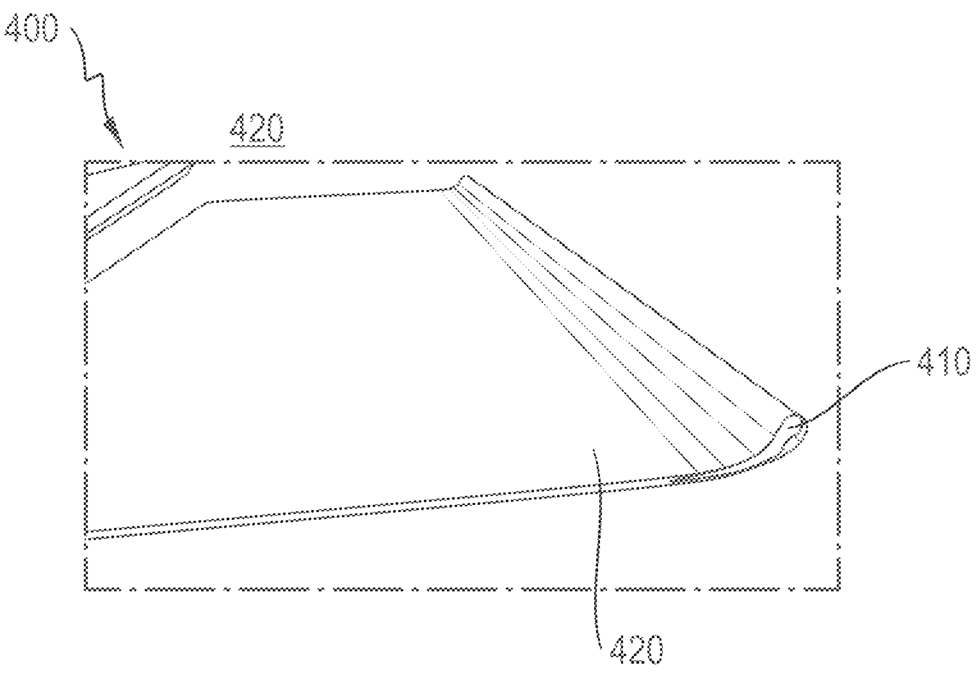
FIG. 7 shows a perspective rear and side view of an alternative fastening element.

An example of a micro-hook fastening element 300 is shown in FIGS. 5 and 6. The micro-hook fastening element 300 has a body with a generally flat, plate-shaped front body portion 310, which is also referred to as a plate part 310. A micro-hook patch 312 with micro-hooks 314 arranged thereon is fastened to the front body part 310. The micro-hook fastening element 300 is configured such that it easily latches into place on a rail 301 of a patient table 305 or the like. In connection with this specification and the preceding claims, any structure that supports a patient is designated as "patient table" 305. These include operating tables, beds, MRI/CT support surfaces and the like.

The micro-hook fastening element 300 comprises an upper side web 332, which extends approximately perpendicularly from the rear face of the front body part 310. A channel 350 is provided in a lower web 340, which extends at a distance from and in parallel under the upper lateral web 332. The channel 350 is approximately 1 cm wide, in order to receive a lower part of the rail 301. The lower web 340 extends along a lower end of the front body part 310 and can have a generally V-shaped cross-sectional shape. The upper lateral web 332 can be arranged at a distance of approximately 3 cm from the bottom surface of the channel 350. The lower web 340 and the upper web 332 are configured such that they can receive frequently used rails 301, which can have a customary rectangular cross-sectional shape and dimensions of, for example, 25 mm×10 mm, 28.5 mm×9.5 mm or 31 mm×7 mm.

The micro-hook patch 312 with micro-hooks 314, which is fastened to the front body part 310, can engage around a lower V-shaped end of the micro-hook fastening element 300 and cover a part of the lower web 340. In order to achieve the desired strength, the use of a micro-hook patch 312 with approximately between 250 and 350 micro-hooks per $cm^2$, in particular with approximately 300 micro-hooks per $cm^2$, has proven advantageous. The micro-hooks 314 can particularly preferably be made of polyamide or polypropylene. The micro-hooks 314 preferably have a height of approximately 0.5 mm, e.g. 0.4 mm. The micro-hook patch 312 can be affixed to the micro-hook fastening element 300 using an adhesive layer 313 advantageously formed from polyurethane.

An elastically deformable rubber strip, in particular a silicone rubber strip 355, can be arranged within the channel 350. When the micro-hook fastening element 300 is fastened to the rail 301, a lower part of the rail 301 is received within the channel 350, while an upper part of the rail 301 is pressed against the upper lateral web 332 by means of the silicone rubber strip 355. The silicone rubber strip 355 is elastically deformed in the process and provides the required clamping force for securely holding the micro-hook fastening element 300 on the rail 301.

The channel 350 is formed along an upper side of the lower web 340 between the plate part 310 and a parallel wall 339. A groove 338 can be formed within a bottom of the channel 350. The deformable silicone rubber strip 355 can have a generally D-shaped hollow cross section, wherein a flat part of the D-shaped cross section rests on a bottom of the channel 350, and a convex part of the D-shaped cross section points upward toward the rail 301. An anchor part 357 can extend vertically into the groove 338 centrally from the flat part of the D-shaped cross section. The deformable silicone rubber strip 355 resembles a D-shaped door sealing strip.

Referring to FIGS. 7 to 11, alternative embodiments to the micro-hook fastening elements 300 are now shown. The alternative fastening element 400 shown includes a micro-hook patch 420, which is wrapped around a keder cord 410. The fastening element 400 can be inserted into a keder rail 450 of a patient table 305. The keder rail 450 runs in the longitudinal direction on the sides of the patient table 305. The keder rail 450 contains at least one groove-shaped cavity 452 (see FIG. 11), which is accessible through an upwardly or laterally directed slot 453. The slot 453 is wide enough to accommodate the thin micro-hook patch 420 in a double layer, and narrow enough to hold its end, wrapped around the keder cord 410, in the groove-shaped cavity 452.

Figure 10:
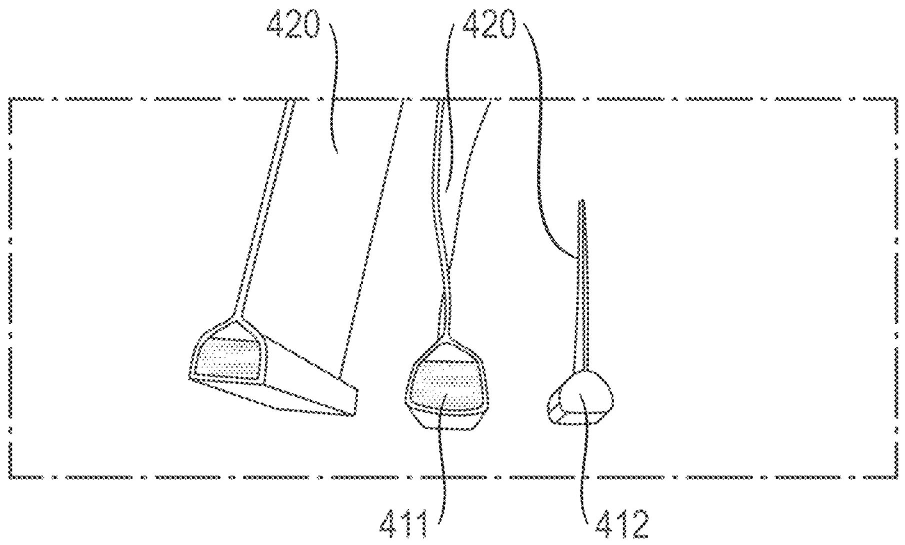
FIG. 10 shows cross sections of alternative configurations of keder cords that can be used in the alternative fastening elements according to FIGS. 7 to 9.

As is shown in FIG. 10, the keder cord 410 can have various cross-sectional shapes. For example, it can have a polygonal, round, oval or D-shaped cross section. A trapezoidal cross section 411 and a generally D-shaped cross section 412 are shown in FIG. 10.

Figure 11:
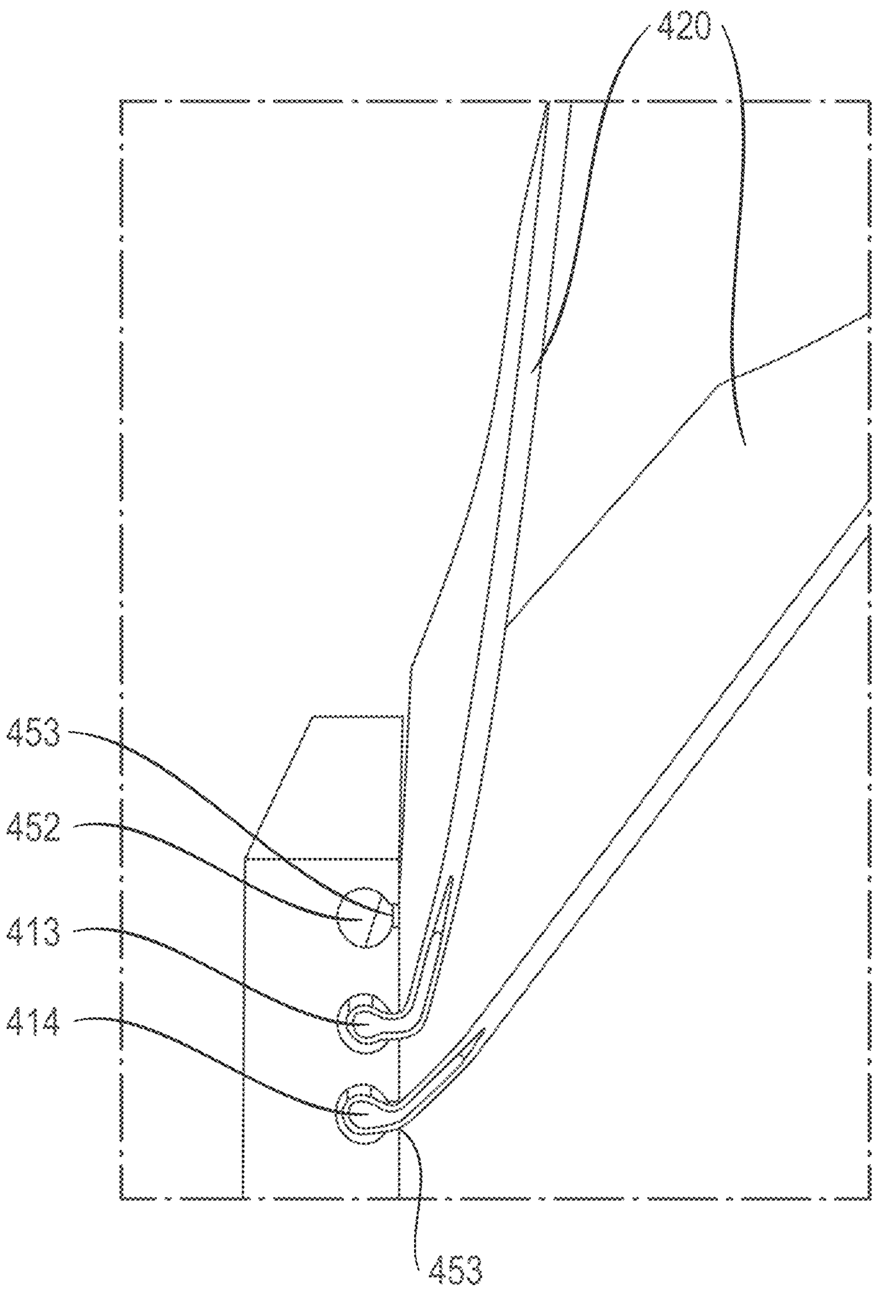
FIG. 11 shows cross sections of alternative embodiments of fastening elements within keder rails.

As is shown in FIG. 11, the keder cord 410 can comprise a generally circular lower part, which is held in the cavity 452 of the keder rail 450, and a thinner upper part, which extends through the slot 453 of the keder rail 450. The upper part of the keder cord 410 can be bent in order to align the micro-hook patch 420 at a defined angle relative to the keder rail 450. As is shown in FIG. 11, a keder cord 413 bent by approximately 90° or a keder cord 414 bent by approximately 45° can be used. Of course, other angles are also possible.

Figure 8:
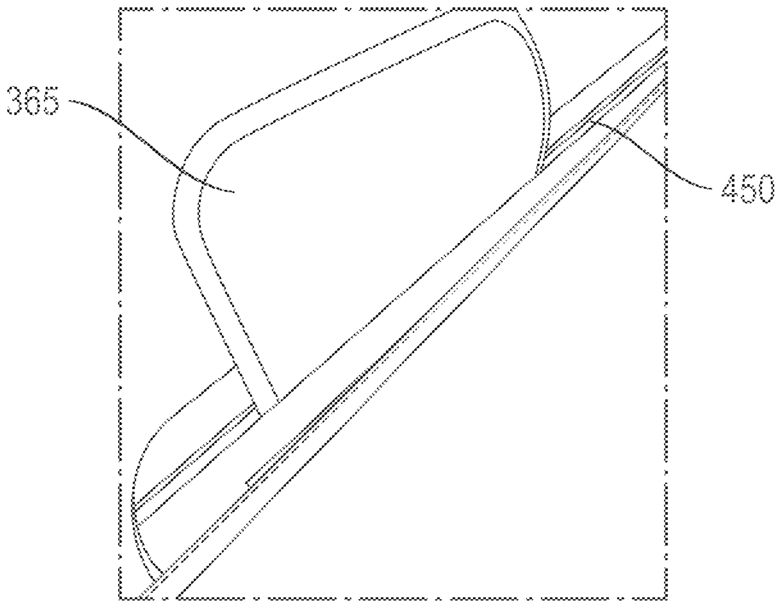
FIG. 8 shows a perspective front and side view showing the alternative fastening element according to FIG. 7 in use when inserted in a keder rail of a patient table.
Figure 9:
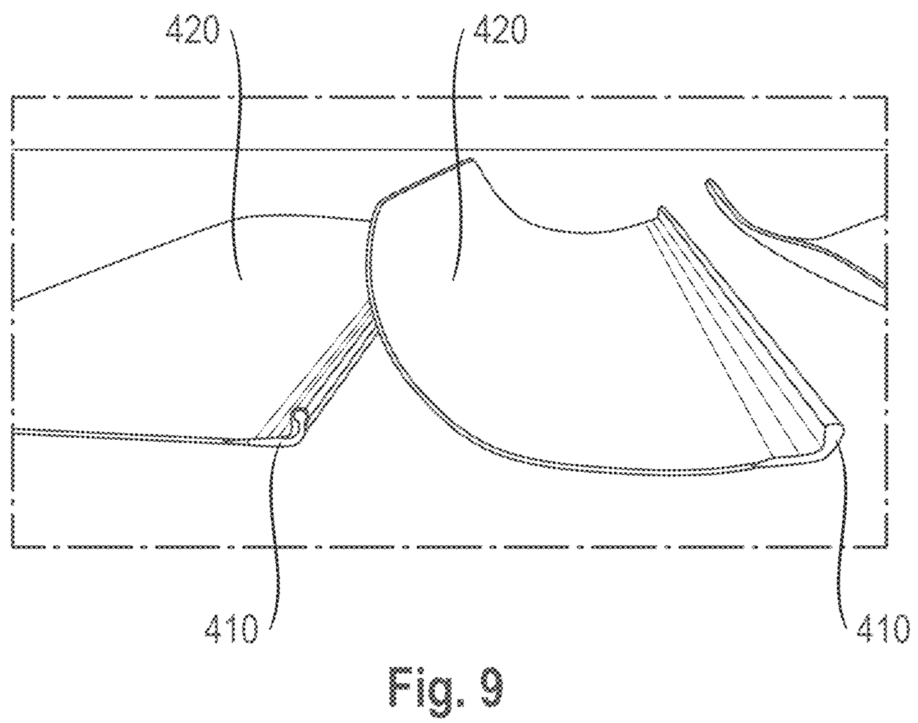
FIG. 9 shows a rear and side view of an alternative fastening element according to FIGS. 7 and 8.

FIG. 8 shows the fastening element 400 with a disposable patch 365 arranged on the inside. Such a disposable patch 365 can be used for various purposes and in combination with any type of fastening element 300 or 400. For example, the disposable patch 365 can be used to protect the micro-hooks 314 of the fastening element 300 or 400 from dirt when not in use. In this case, the fastening element 300, 400 can be supplied together with a disposable patch 365. The disposable patch 365 protects the micro-hooks 314 during transport and is only removed shortly before use.

Alternatively, as is shown in FIG. 8, the disposable patch 365 can also be used on the patient-side face of the fastening element 400, in order to prevent direct contact between the micro-hooks and a patient.

Figure 12:
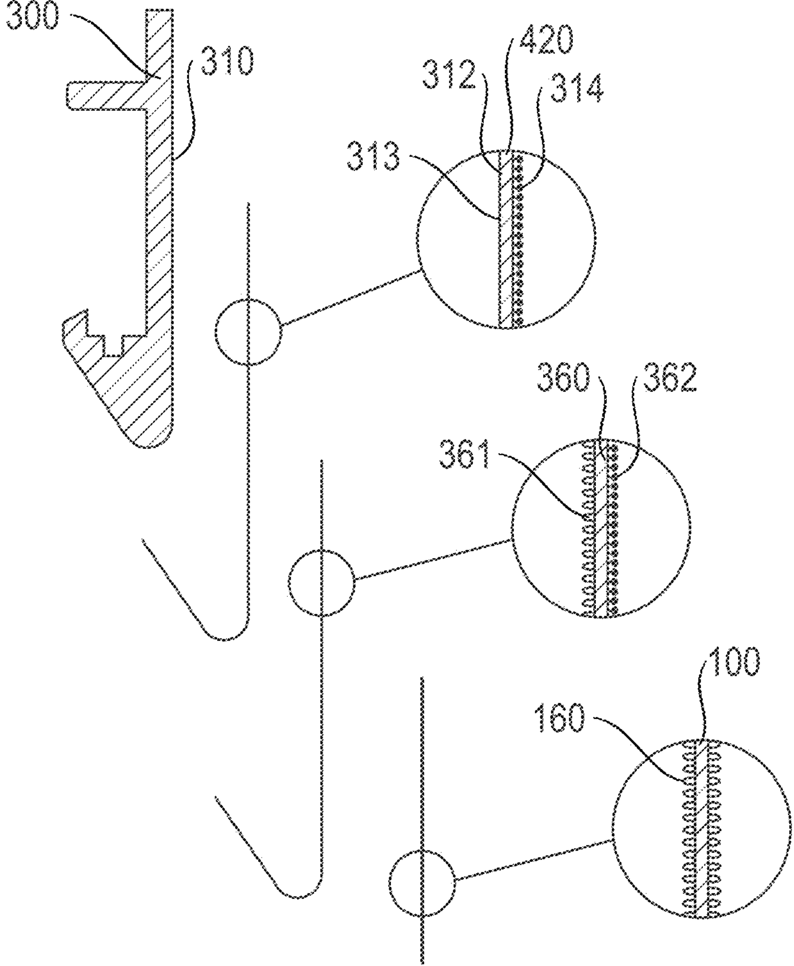
FIG. 12 shows an exploded sectional view of a fastening element with an anchor patch, a disposable patch and the patient immobilization device.

FIG. 12 shows a cross-sectional view of a fastening element 300 in an exploded view. A micro-hook patch 312 with micro-hooks 314 is fastened to the front body part 310 of the micro-hook fastening element 300. Here, the micro-hook patch 312 is affixed to the front body part 310 of the micro-hook fastening element 300 by an adhesive layer 313. The micro-hooks 314 are formed on an opposite, outwardly facing side of the micro-hook patch 312. The micro-hooks 314 can generally be mushroom-shaped elements that are suitable for engaging in loops 160 of the nonwoven fabric of the patient immobilization device 100 and for clamping themselves firmly therein.

The micro-hook patch 312 can be permanently affixed to the front body part 310 of the micro-hook fastening element 300 and can then also be designated as an anchor patch 312. The micro-hook patch 312 is not easily exchangeable in this case.

For some uses, it is preferable to use disposable patches that do not need to be cleaned. Such a disposable patch 360 is shown in FIG. 12. The disposable patch 360 has, on its inner face, a layer of microfiber loops 361, similar to those of the patient immobilization device 100, 101. The disposable patch 360 has a micro-hook layer 362 on its outer face, the micro-hooks corresponding to those of the anchor patch 312.

The disposable patch 360 can thus form an intermediate layer between the anchor patch 312 and the patient immobilization device 100. More than one disposable patch 360 can be used in order to form a sandwich structure in which several disposable patches 360 are arranged between the anchor patch 312 of the micro-hook fastening element 300 and the patient immobilization device 100. After each use, the patient immobilization device 100 and the outermost disposable patch 360 can be discarded, as a result of which a clean and possibly also immediately sterile environment is created for the next patient.

The invention allows a patient immobilization device 100, 101 to be handled in a simple and uncomplicated manner, which is very advantageous in the clinical or medical field. By virtue of its material properties, the planar element 105 with its multiple arms 120, 130 can be brought into engagement directly with the micro-hooks 314 on the micro-hook fastening element 300, on the micro-hook patch or anchor patch 312 or 420, and fixed. Since the aforementioned fastening elements having the micro-hooks 314 are displaceable as required on the rail 301 or on the groove-shaped cavity 452 of a patient table 305, the conditions for immobilizing a patient or individual parts of the body of a patient can be variably established in an extremely short time.

Although the present invention has been described with reference to illustrative embodiments, it will be readily apparent to a person skilled in the art that the invention is not limited to the disclosed or depicted embodiments, but on the contrary is intended to cover numerous other modifications, substitutions, variations and far-reaching equivalents contained within the spirit and scope of the following claims. In particular, all of the illustrated and described details of the various embodiments can be combined or interchanged with one another as desired.

LIST OF REFERENCE SIGNS

100 patient immobilization device
101 patient immobilization device (in folded state)
105 (planar) element
110 elongate middle part
112 perforation
113 perforation
120 left arm
130 right arm
140 longitudinal gap (between 120 or 130)
150 transition (to 140)
160 loops (on 100, 101)
201 arrow
202 arrow
203 arrow
204 arrow
209 part (of 110)
211 part (of 120)
212 part (of 120)
213 part (of 130)
214 part (of 130)
219 part (of 110)
300 micro-hook fastening element
301 rail
305 patient table
310 front body part/plate part
312 micro-hook patch/anchor patch
313 adhesive layer
314 micro-hook
332 upper lateral web
338 groove
339 wall
340 lower web
350 channel
355 rubber strip/silicone rubber strip
357 anchor part
360 disposable patch
361 microfiber loops
362 micro-hook layer
365 disposable patch
400 fastening element
410 keder cord
411 cross section (trapezoidal)
412 cross section (D-shaped)
413 keder cord (bent 90°)
414 keder cord (bent 45°)
420 micro-hook patch
450 keder rail
452 cavity/keder groove
453 slot
P patient

The invention claimed is:

1. A patient immobilization device (100, 101) having a planar element (105) made of a nonwoven fabric, wherein the planar element is formed of an elongate middle part (110) and a multiplicity of arms (120, 130) which extend integrally and laterally from both sides of the middle part (110), wherein the nonwoven fabric forms loops (160) for engagement with mushroom-shaped micro-hooks (314), wherein at least two arms (120, 130) extend from each side of the elongate middle part (110) and every two adjacent arms (120, 130) of the multiplicity of arms (120, 130) are separated by a longitudinal gap (140) having a semicircular transition (150) at the middle part (110) and a width of between 1 cm and 10 cm.

2. A system comprising a patient immobilization device (100, 101) as claimed in claim 1 and a multiplicity of micro-hook fastening elements (300) or fastening elements (400), which are fastenable on at least one side of a patient table (305).

3. The system as claimed in claim 2, in which each of the micro-hook fastening elements (300) comprises the following:

a body part (310) having a multiplicity of micro-hooks (314) arranged thereon;

a upper web (332); and a lower web (340), wherein the upper web (332) and the lower web (340) are configured such that a rail (301) of a patient table (305) can be clamped between them.

4. The system as claimed in claim 3, in which the lower web (340) has a channel (350), which is configured such that it supports a lower part of the rail (301) of the patient table (305), and moreover has an elastically deformable rubber strip (355), which can be arranged within the channel (350).

5. The system as claimed in claim 4, further comprising disposable patches (365), which are arranged between the patient immobilization device (100) and the micro-hook fastening elements (300), wherein the disposable patches (365) have fabric loops which are arranged on the inner face of the disposable patches (365) and micro-hooks (314) which are arranged on the outer face of the disposable patches (365).

6. The system as claimed in claim 3, further comprising disposable patches (365), which are arranged between the patient immobilization device (100) and the micro-hook fastening elements (300), wherein the disposable patches (365) have fabric loops which are arranged on the inner face of the disposable patches (365) and micro-hooks (314) which are arranged on the outer face of the disposable patches (365).

7. The system as claimed in claim 2, in which one or more arms (120, 130) of the patient immobilization device (100, 101) are held by micro-hooks (314) which are arranged on parts (310; 312; 420) of the micro-hook fastening elements (300) or fastening elements (400).

8. The system as claimed in claim 7, further comprising disposable patches (365), which are arranged between the patient immobilization device (100) and the micro-hook fastening elements (300), wherein the disposable patches (365) have fabric loops which are arranged on the inner face of the disposable patches (365) and micro-hooks (314) which are arranged on the outer face of the disposable patches (365).

9. The system as claimed in claim 7, in which each of the micro-hook fastening elements (300) has a removable disposable patch (360), which engages in the micro-hooks (314) of the micro-hook fastening elements (300).

10. The system as claimed in claim 2, in which each of the micro-hook fastening elements (300) or fastening elements (400) has a keder cord (410; 413; 414) and a micro-hook patch (420) wrapped around the keder cord (410; 413; 414).

11. The system as claimed in claim 10, in which the keder cord (410; 413; 414) has a lower part with a cross-sectional diameter greater than the diameter of a keder groove (452) of a patient table (305) that forms a cavity (452), and an upper part having a width that is smaller than the width of a slot (453) of the keder groove (452).

12. The system as claimed in claim 11, in which an upper part of the keder cord (410; 413; 414) that passes through the slot (453) is bent between 45 degrees and 90 degrees.

13. The system as claimed in claim 2, further comprising disposable patches (365), which are arranged between the patient immobilization device (100) and the micro-hook fastening elements (300), wherein the disposable patches (365) have fabric loops which are arranged on the inner face of the disposable patches (365) and micro-hooks (314) which are arranged on the outer face of the disposable patches (365).

14. The system as claimed in claim 2, in which each of the micro-hook fastening elements (300) has a removable disposable patch (360), which engages in the micro-hooks (314) of the micro-hook fastening elements (300).

15. The patient immobilization device (100) as claimed in claim 1 in a folded storage position, wherein each of the arms (120, 130) is folded laterally onto the elongate middle part (110), and wherein parts of the elongate middle part (110), with the arms (120, 130) folded laterally thereon, are in turn folded onto each other in the longitudinal direction.

16. The patient immobilization device (100, 101) as claimed in claim 15, in which each arm (120, 130) is additionally folded laterally onto itself and folded laterally onto the elongate middle part (110).

17. A system comprising a patient immobilization device (100, 101) as claimed in claim 16 and a multiplicity of micro-hook fastening elements (300) or fastening elements (400), which are fastenable on at least one side of a patient table (305).

18. A system comprising a patient immobilization device (100, 101) as claimed in claim 15 and a multiplicity of micro-hook fastening elements (300) or fastening elements (400), which are fastenable on at least one side of a patient table (305).

19. A method for securing a patient on a patient table, comprising the following method steps:

providing the patient immobilization device (100, 101) as claimed in claim 1;

placing the patient immobilization device (100; 110) on the patient P; and fastening two or more arms (120; 130) of the patient immobilization device (100) to micro-hook fastening elements (300) or fastening elements (400) on opposite sides of a patient table (305).

20. The method as claimed in claim 19, further comprising:

selectively removing a part of the patient immobilization device (100) in order to create an access opening for performing a medical intervention on the patient.

21. The patient immobilization device of claim 1, wherein a multiplicity of arms (120, 130) and extended middle part (11) are a single unwoven fabric sheet with longitudinal gaps (140) cut out from the single unwoven fabric sheet between adjacent arms of the multiplicity of arm (120, 130).

* * * * *